United States Patent
Denison et al.

(10) Patent No.: US 11,511,115 B2
(45) Date of Patent: *Nov. 29, 2022

(54) SIMULTANEOUS PHYSIOLOGICAL SENSING AND STIMULATION WITH SATURATION DETECTION

(71) Applicant: Medtronic, Inc., Minneapolis, MN (US)

(72) Inventors: Timothy J. Denison, Minneapolis, MN (US); Pedram Afshar, San Francisco, CA (US); Scott R. Stanslaski, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1057 days.

This patent is subject to a terminal disclaimer.

(21) Appl. No.: 16/110,439

(22) Filed: Aug. 23, 2018

(65) Prior Publication Data

US 2019/0015665 A1    Jan. 17, 2019

Related U.S. Application Data

(63) Continuation of application No. 14/725,998, filed on May 29, 2015, now Pat. No. 10,080,898.

(51) Int. Cl.
*A61N 1/00* (2006.01)
*A61N 1/36* (2006.01)
(Continued)

(52) U.S. Cl.
CPC .......... *A61N 1/36135* (2013.01); *A61B 5/374* (2021.01); *A61B 5/7221* (2013.01);
(Continued)

(58) Field of Classification Search
CPC ............ A61N 1/36135; A61N 1/36067; A61N 1/0534; A61B 5/374; A61B 5/7221;
(Continued)

(56) References Cited

U.S. PATENT DOCUMENTS

| 4,525,677 A | 6/1985 | Rorden |
| 4,981,141 A | 1/1991 | Seagalowitz |

(Continued)

FOREIGN PATENT DOCUMENTS

| WO | 2007058950 A2 | 5/2007 |
| WO | 2013142944 A1 | 10/2013 |

(Continued)

OTHER PUBLICATIONS

"PGA Manual", Multichannel Systems, Nov. 10, 2010, 24 pages.
(Continued)

*Primary Examiner* — David J. McCrosky
*Assistant Examiner* — Reilly A Carlton
(74) *Attorney, Agent, or Firm* — Shumaker & Sieffert, P.A.

(57) ABSTRACT

Systems and method may be used for interfacing with a patient. Systems may include a plurality of electrodes in electrical communication with a processor. The processor may be configured to receive sense signals from electrodes and to determine the reliability of the received signal. A test tone signal comprising a test tone frequency may be applied, and the magnitude of the test tone frequency may be analyzed in the received signal. If it is determined that the magnitude of the test tone frequency is below a threshold, the system may take action, such as lowering the gain on an amplifier. Stimulation signals may be applied to the patient at a stimulation frequency simultaneously with one or both of receiving sense signals and providing the test tone signal.

20 Claims, 6 Drawing Sheets

(51) Int. Cl.
*A61B 5/00* (2006.01)
*A61B 5/374* (2021.01)
*A61N 1/05* (2006.01)

(52) U.S. Cl.
CPC ........ *A61N 1/36067* (2013.01); *A61B 5/4082* (2013.01); *A61B 5/4836* (2013.01); *A61N 1/0534* (2013.01)

(58) Field of Classification Search
CPC ..... A61B 5/4082; A61B 5/4836; A61B 5/372; A61B 5/0048; A61B 5/1104; A61B 5/1106; A61B 5/38; A61B 5/383; A61B 5/686; A61B 5/4076
See application file for complete search history.

(56) References Cited

U.S. PATENT DOCUMENTS

| | | |
|---|---|---|
| 5,368,041 A | 11/1994 | Shambroom |
| 5,381,804 A | 1/1995 | Shambroom |
| 5,776,167 A | 7/1998 | Levine et al. |
| 6,032,060 A | 2/2000 | Carim et al. |
| 6,463,411 B1 | 10/2002 | Li et al. |
| 6,493,576 B1 | 12/2002 | Dankwart-Eder |
| 7,385,443 B1 | 6/2008 | Denison |
| 7,953,230 B2 | 5/2011 | Nadjar et al. |
| 8,068,905 B2 | 11/2011 | Freeman et al. |
| 8,121,694 B2 | 2/2012 | Molnar et al. |
| 8,248,137 B2 | 8/2012 | Peuscher |
| 8,260,412 B2 | 9/2012 | Krause et al. |
| 8,359,083 B2 | 1/2013 | Clark et al. |
| 8,406,893 B2 | 3/2013 | Krause et al. |
| 8,428,733 B2 | 4/2013 | Carlson et al. |
| 8,504,154 B2 | 8/2013 | Wanasek |
| 8,538,512 B1 * | 9/2013 | Bibian ................ A61B 5/4839 600/545 |
| 8,577,457 B2 | 11/2013 | Miller et al. |
| 8,798,751 B2 | 8/2014 | Spear et al. |
| 8,849,390 B2 | 9/2014 | Echauz et al. |
| 8,868,148 B2 | 10/2014 | Engelbrecht et al. |
| 9,649,492 B2 | 5/2017 | Li et al. |
| 10,080,898 B2 * | 9/2018 | Denison ............... A61B 5/7221 |
| 2002/0165458 A1 | 11/2002 | Carter et al. |
| 2004/0210148 A1 | 10/2004 | VanEss |
| 2005/0010265 A1 | 1/2005 | Baru et al. |
| 2006/0095092 A1 * | 5/2006 | Drew .................. A61B 5/0031 607/32 |
| 2008/0132979 A1 | 6/2008 | Gerber |
| 2008/0243022 A1 | 10/2008 | Donnett et al. |
| 2009/0045886 A1 | 2/2009 | Gruchalla |
| 2009/0082691 A1 | 3/2009 | Denison et al. |
| 2009/0192556 A1 | 7/2009 | Wu et al. |
| 2010/0010369 A1 | 1/2010 | Pomfreti et al. |
| 2010/0023084 A1 | 1/2010 | Gunderson |
| 2010/0100153 A1 | 4/2010 | Carlson et al. |
| 2011/0001497 A1 | 1/2011 | Chetelat et al. |
| 2011/0040546 A1 | 2/2011 | Gerber et al. |
| 2011/0125214 A1 | 5/2011 | Goetz et al. |
| 2011/0201944 A1 | 8/2011 | Higgins et al. |
| 2011/0257708 A1 | 10/2011 | Kramer et al. |
| 2012/0065536 A1 | 3/2012 | Causevic et al. |
| 2012/0109258 A1 | 5/2012 | Cinbis et al. |
| 2012/0194268 A1 | 8/2012 | Chang et al. |
| 2012/0277820 A1 | 11/2012 | Wu et al. |
| 2012/0296444 A1 | 11/2012 | Greenberg et al. |
| 2013/0006324 A1 | 1/2013 | Bradley |
| 2013/0131755 A1 | 5/2013 | Panken et al. |
| 2013/0218232 A1 | 8/2013 | Giftakis et al. |
| 2013/0328572 A1 | 12/2013 | Wang et al. |
| 2014/0277282 A1 | 9/2014 | Jaax |
| 2015/0352085 A1 | 12/2015 | During |
| 2016/0067497 A1 | 3/2016 | Levine et al. |
| 2016/0346534 A1 | 12/2016 | Isaacson et al. |

FOREIGN PATENT DOCUMENTS

| | | | |
|---|---|---|---|
| WO | 2014043739 A1 | 3/2014 | |
| WO | 2014167418 A2 | 10/2014 | |
| WO | WO-2015069632 A1 * | 5/2015 | ............. A61B 3/112 |

OTHER PUBLICATIONS

Afshar, "A transnational platform for protyping closed-loop neuromodulation systems," Frontiers in Neural Circuits, vol. 6, Jan. 22, 2013, 15 pp.

Baker, "A psychophysically derived model of signal combination predicts neural responses in two stimulus domains," Journal of Vision, vol. 14, No. 10, article 1180, Aug. 22, 2014, 1 pp.

Galvan et al., "Long-Term Frequency Tuning of Local Field Potentials in the Auditory Cortex of the Waking Guinea Pig," Journal of the Association for Research in Otolaryngology, May 14, 2001, 17 pages.

Goetz et al., "A Novel Model Incorporating Two Variability Sources for Describing Motor Evoked Potentials," Brain Stimulation; May 2, 2014, 12 pages.

Goyal, "Automatic gain contro in burst communications systems," RF Design, Feb. 2000, 9 pp.

Oh et al., Multi-frequency EIT system with radially symmetric architecture: KHU Mark 1, Jun. 26, 2007, 14 pages.

Response to Communication Pursuant to Rules 161(1) and 162 EPC dated Aug. 8, 2018 from counterpart European Application No. 16714711.5, 11 pp.

Stanslaski, "Design and Validation of a Fully Implantable, Chronic, Closed-Loop Neuromodulation Device with Concurrent Sensing and Stimulation," IEEE, vol. 20, No. 4, Jul. 4, 2012, pp. 410-421.

Wang, "Design of a 32-Channel EEG System for Brain Control Interface Applications," Apr. 10, 2012, 10 pages.

Prosecution History from U.S. Appl. No. 14/725,998 dated from Jul. 31, 2017 through Jul. 2, 2018, 66 pp.

* cited by examiner

SIMULTANEOUS PHYSIOLOGICAL SENSING AND STIMULATION WITH SATURATION DETECTION

This application is a continuation of U.S. application Ser. No. 14/725,998, filed May 29, 2015, the entire contents of which are incorporated by reference herein.

BACKGROUND

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement or other nervous disorders.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may define characteristics of the electrical stimulation waveform to be delivered. Where electrical stimulation is delivered in the form of electrical pulses, for example, the parameters may include an electrode combination, an amplitude, which may be a current or voltage amplitude, a pulse width, a pulse shape, and a pulse rate.

The sensing and monitoring of electrical signals from the patient's nervous system can be an important aspect of therapeutic and diagnostic procedures. However, such sensing and monitoring presents challenges. Neurological bioelectrical signals have relatively small magnitudes compared to those in other areas of the body, such as cardiac signals, for example. Accordingly, these signals are typically amplified for analysis. However, the application of electrical stimulation obscures these neurological bioelectrical signals during the application of the stimulation. For example, saturation of the amplifiers results, thereby rendering the sensed signal unreliable. As a result, bioelectrical signals are not typically measured during stimulation. Instead, sensing electrodes are often blocked during stimulation and re-enabled after stimulation in an attempt to observe the effect of the stimulation pulse. However, such blocking and re-enabling practice can result in missing useful information that occurs during the stimulation itself.

SUMMARY

Aspects of the present disclosure are generally directed to systems and methods for interfacing with a patient. Methods can include receiving a sense signal from a patient. The sense signal may be processed to produce a process signal. Methods may include monitoring at least one reliability signal indicative of the reliability of the sense signal or processed signal. In some examples, in the event that the reliability signal meets at least one predetermined criterion, the method includes performing at least one action to improve the reliability of the sense signal or processed signal.

In some examples, methods can include applying a test tone signal with frequency content comprising a test frequency. Methods can include monitoring the magnitude of the test frequency in the sense signal or processed signal and comparing the magnitude of the processed signal to a threshold. In some such examples, the reliability signal may include the magnitude of the test frequency in the processed signal or sense signal.

Some methods can include applying a stimulation signal comprising a stimulation frequency. The stimulation signal may be applied simultaneously with receiving a sense signal, and in some examples, both may be performed simultaneously with applying a test tone signal. In some examples, the stimulation frequency, the test frequency, and the frequency content of signals of interest in the sense signal are distinct. For example, in some methods, the stimulation frequency may be within a first frequency band, signal of interest may include frequency content within a second band separate from the first, and the test frequency may be outside of both of the first and second frequency bands.

Systems according to embodiments of the disclosure may include a processor and a plurality of electrodes for interfacing with a patient. In some examples, the processor may be configured to provide one or both of a simulation signal and a test tone signal to the patient via one or more electrodes. The system can include at least one sense electrode configured to receive a sense signal from the patient. In some examples, the system includes an amplifier for amplifying the sense signal and a processor configured to receive an amplified signal from the amplifier. The processor can be configured to determine the magnitude of the test frequency in the amplified signal and compare the magnitude to a threshold. If the magnitude falls below the threshold, the processor may be configured to lower the gain of the at least one amplifier. In some systems, the stimulation signal and test tone signal may be applied simultaneously while receiving a sense signal. In some examples, the test tone signal may be applied during a sensing procedure without stimulation being applied. Systems may include additional or alternative components to a test tone for determining the reliability of a sensed or processed signal.

DETAILED DESCRIPTION

Figure 1:
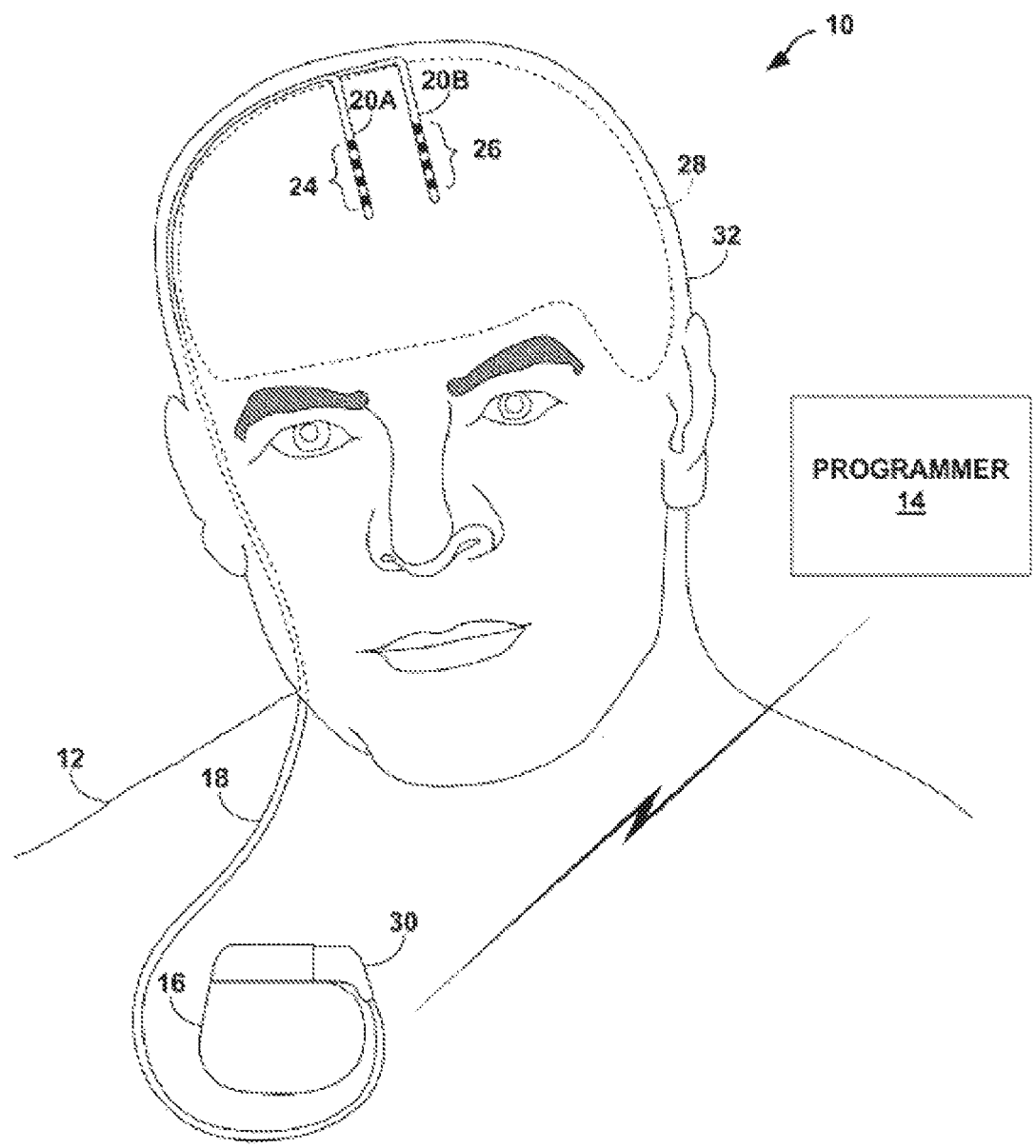
FIG. 1 is a conceptual diagram illustrating an example of a deep brain stimulation (DBS) system.

FIG. 1 is a conceptual diagram illustrating an example nervous interface system 10 that electrically interfaces with the nervous system of a patient. In some examples, the nervous interface system 10 includes a therapy system that delivers therapy to control a patient condition, such as a movement disorder or a neurodegenerative impairment of patient 12. In other examples, the interface system 10 can be used as a diagnostic instrument for receiving electrical signals from the nervous tissue of the patient 12. Patient 12 ordinarily will be a human patient. In some cases, however, therapy system 10 may be applied to other mammalian or non-mammalian non-human patients. While movement disorders and neurodegenerative impairment are primarily referred to herein, in other examples, therapy system 10 may provide therapy to manage symptoms of other patient conditions, such as, but not limited to, seizure disorders, neurodegenerative impairment or psychological disorders.

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

The interface system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to interface with a tissue site within brain 28, such as a deep brain site under the dura mater of brain 28 of patient 12. In some examples, electrodes can be configured to interface with one or more regions of brain 28, such as the subthalamic nucleus, globus pallidus or thalamus. Stimulation system can be configured to deliver electrical stimulation to such regions, which may be an effective treatment to manage movement disorders, such as Parkinson's disease. It will be appreciated that in further examples, interface system 10 can be positioned to interface with a nervous tissue site in a region separate from the patient's brain, or with other physiological systems of the patient such as the muscular system.

In the illustrated embodiment, IMD 16 includes a therapy module that includes a stimulation generator that may generate and deliver electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination. It will be appreciated that in other embodiments, such as in an exemplary diagnostic instrument, IMD 16 need not include a therapy module.

The IMD 16 can include a sensing module 46 configured to sense bioelectrical or other electrical signals within the brain 28 via a subset of electrodes 24, 26 of leads 20A and 20B, respectively. While two leads 20A, 20B are shown in the illustrated embodiment, it will be appreciated that embodiments of the invention are not limited to two leads, but may include any appropriate number of leads. For example, various embodiments can include a single lead having a plurality of electrodes or a plurality of leads each having at least one electrode. Generally, each lead of a plurality of leads need not include the same number of electrodes. The subset of electrodes 24, 26 that are used to sense such signals within the brain 28 may be referred to as sense electrodes, a sense electrode combination, or at least one sense electrode. Examples of bioelectrical brain signals include, but are not limited to, electrical signals generated from local field potentials within one or more regions of brain 28, an electroencephalogram (EEG) signal or an electrocorticogram (ECoG) signal.

In stimulation systems, electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

In some examples, stimulation signals can include signal components located within one or more frequency ranges (e.g., within a first frequency band). In some examples, the stimulation signals can include components in multiple frequency bands. For instance, a signal having a component with frequency F may comprise signal components having frequencies at one or both of harmonics and sub-harmonics of F. In some embodiments, the stimulation signal can include components located within a first frequency range. In some such examples, the first frequency range may include any combination of a primary stimulation frequency, one or more harmonics, and one or more sub-harmonics. Additionally or alternatively, the first frequency range may include first frequency ranges, wherein the frequency content of a signal may include components in one or more overlapping or disjoint ranges.

In various embodiments, IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order deliver electrical stimulation to one or more regions of brain 28, which may be selected based on the patient condition or disorder controlled by therapy system 10. Other lead 20 and IMD 16 implant sites are contemplated. For example, IMD 16 may be implanted on or within cranium 32, in some examples. Or leads 20 may be implanted within the same hemisphere or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. In an exemplary stimulating system interfacing with a patient's brain, leads 20 may be positioned to deliver electrical stimulation to one or more target tissue sites within brain 28 to manage patient symptoms associated with a movement disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

Example techniques for delivering therapy to manage a movement disorder are described in U.S. Pat. No. 8,121,694, entitled, "THERAPY CONTROL BASED ON A PATIENT MOVEMENT STATE," which was filed on Sep. 25, 2008, which is incorporated herein by reference in its entirety. In some examples described by U.S. patent application Ser. No. 12/237,799 to Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12 initiate movement or maintain movement, and upon detecting a rest state of patient 12, therapy delivery may be deactivated or otherwise modified.

In the example shown in FIG. 1, electrodes 24, 26 of leads 20 are shown as ring electrodes. Ring electrodes may be used in patient interface applications because they are relatively simple to program and are capable of electrically communicating with any tissue adjacent to electrodes 24, 26. For instance, in a stimulation system interfacing with a patient's brain, ring electrodes are capable of delivering an electrical field to any tissue adjacent to electrodes 24, 26. In other examples, electrodes 24, 26 may have different configurations. For examples, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. As discussed, additionally or alternatively, the system can include a number other than two leads 20, each including more or fewer electrodes than shown.

In this manner, electrical stimulation may be directed to a specific direction from leads 20 to enhance therapy efficacy and reduce possible adverse side effects from stimulating a large volume of tissue. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12.

In general, the subsets of electrodes 24, 26 that are used as stimulation electrodes and as sense electrodes can be selected by a variety of selection processes, some of which are described in the commonly-assigned U.S. Pat. No. 8,428,733 to Carlson et al., entitled, "STIMULATION ELECTRODE SELECTION," which was filed on Sep. 21, 2009 and is incorporated herein by reference in its entirety. In some embodiments, any electrodes 24, 26 or electrode combinations, including an electrode on the housing of IMD 16, are capable of providing electrical signals to and receiving signals from the brain 28 or other nervous tissue of the patient. In other embodiments, such as diagnostic systems, electrodes 24, 26 or electrode combinations can be capable of receiving signals from proximate nervous tissue of the patient.

External programmer 14 wirelessly communicates with IMD 16 as needed to provide or retrieve therapy or diagnostic information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate through the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

In therapeutic stimulation systems, the clinician may also store therapy programs within IMD 16 with the aid of programmer 14. During a programming session, the clinician may determine one or more therapy programs that may provide efficacious therapy to patient 12 to address symptoms associated with a patient condition, such as a movement disorder. In some examples, the programs may deliver stimulation in a closed-loop manner, such as in response to one or more different patient states, such as a sleep state, movement state or rest state. For example, in stimulation systems, the clinician may select one or more stimulation electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., muscle activity or muscle tone). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

In some examples, a therapy system may be implemented to provide chronic stimulation therapy to patient 12 over the course of several months or years. However, a therapy system may also be employed on a trial basis to evaluate therapy before committing to full implantation. If implemented temporarily, some components of stimulation system may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates the stimulation system provides effective treatment to patient 12, the clinician may implant a chronic stimulator within patient 12 for relatively long-term treatment In other examples, an interface system 10 may be implemented for diagnostic or monitoring purposes over a period of time. A temporary system may be used for a patient undergoing a one-time diagnostic procedure. However, if a patient will require repeated or periodic monitoring, a purely diagnostic system 10 may be implanted. In some further examples, an implanted system for diagnostic purposes may be reprogrammed, for example, by programmer 14, to enable a stimulation program to operate via the implanted system.

Figure 2:
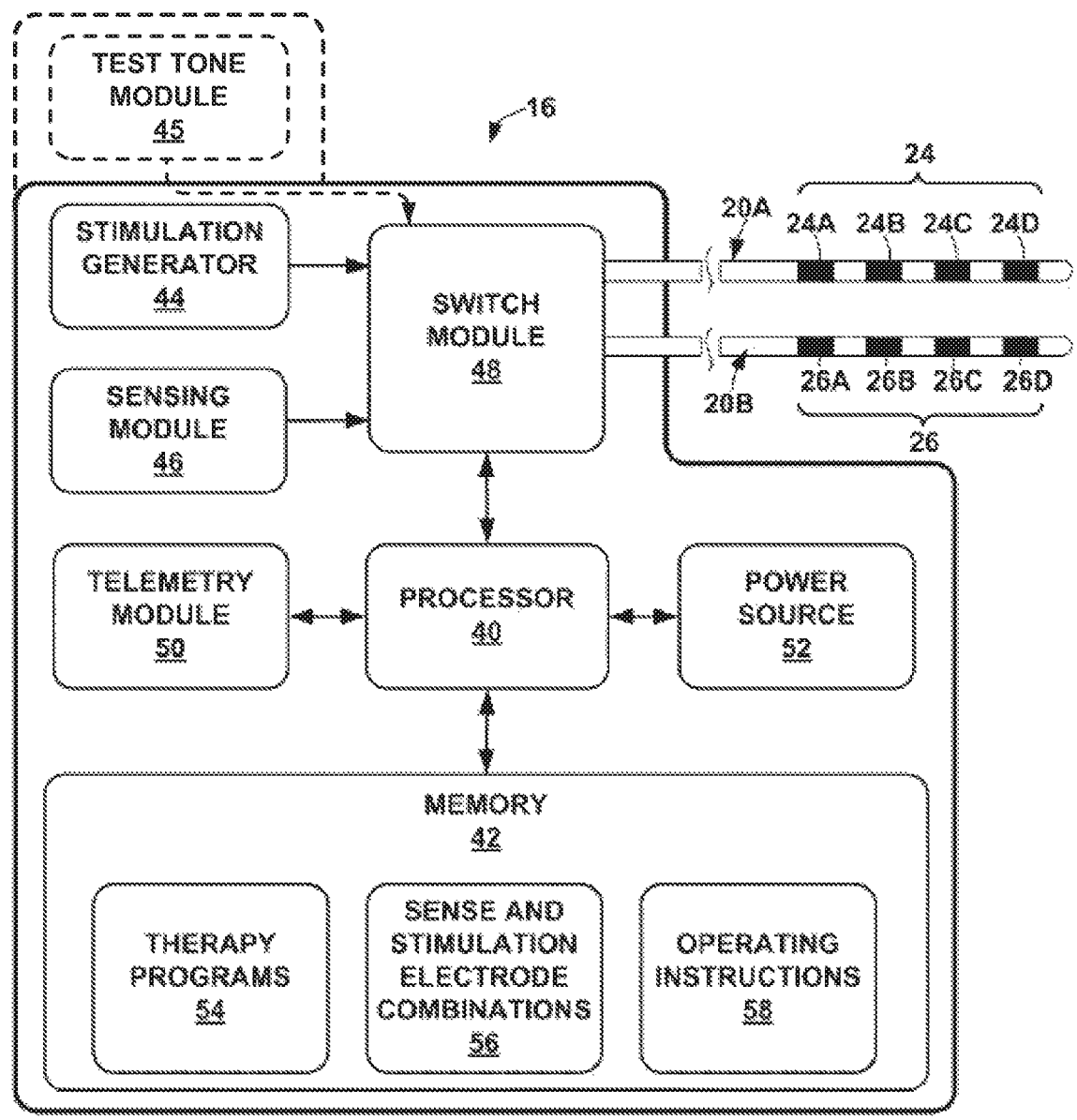
FIG. 2 is a functional block diagram illustrating components of an example medical device.

FIG. 2 is a functional block diagram illustrating components of an example IMD 16 for a stimulating system. In the example shown in FIG. 2, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

As previously discussed, in the example shown in FIG. 2, memory 42 may store therapy programs 54, sense electrode combinations and associated stimulation electrode combinations 56, and operating instructions 58 in separate memories within memory 42 or separate areas within memory 42. In other cases, sense and stimulation electrode combinations need not be associated with one another. In addition, in some examples, memory 42 may store a bioelectrical brain signal sensed via at least some of the stored sense electrode combinations and/or one or more frequency band characteristics of the bioelectrical brain signals. Each stored therapy program 52 defines a particular program of therapy in terms of respective values for electrical stimulation parameters, such as a stimulation electrode combination, electrode polarity, current or voltage amplitude, pulse width, and pulse rate. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Stimulation may be delivered in a bi-polar manner between two or more electrodes 24, 26 on leads 20, or may instead be delivered in a unipolar manner between an electrode on leads 20 and a common reference point. In some examples, the housing (or "can") of IMD 16 can function as a common reference. Similarly, sensing may be performed in a bi-polar manner between two electrodes 24, 26 on leads 20, or in a unipolar manner between an electrode 24, 26 on leads 20 and a common reference point such as the housing of IMD 16. Operating instructions 58 guide general operation of IMD 16 under control of processor 40, and may include instructions for measuring the impedance of electrodes 24, 26 and/or determining the distance between electrodes 24, 26.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include:

1. Frequency: the stimulation signal can include signal components within a first range of frequencies, for example, between approximately 0 Hz and approximately 500 Hz, between approximately 100 Hz and approximately 500 Hz, between approximately 120 Hz and approximately 200 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 may generate electrical stimulation signals in accordance with the electrical stimulation parameters noted above. Other ranges of therapy parameter values may also be useful, and may depend on, for example, one or both of the therapy being provided and the target stimulation site within patient 12, which may or may not be within brain 28. While stimulation pulses are described, stimulation signals may be of any form, such as continuous-time signals (e.g., sine waves) or the like. In general, a stimulation signal may include any arbitrarily shaped waveform. In some examples, the efficacy of the stimulation waveform may be dependent on the location in the patient's body, the contact with the patient's nervous tissue, or other factors. In some embodiments, the waveform of the stimulation signal may be selected based on particular factors of a patient.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 herein may be embodied as firmware, hardware, software or any combination thereof. Processor 40 controls stimulation generator 44 according to therapy programs 52 stored in memory 42 to apply particular stimulation parameter values specified by one or more of programs, such as amplitude, pulse width, and pulse rate. In general, as used herein, the processor may be configured to perform actions such as providing or receiving signals, pulses, and the like. In various embodiments, the processor 40 is capable of performing such functions directly. Additionally or alternatively, the processor 40 may perform such actions indirectly by causing another component, such as stimulation generator 44 or the like, to perform such functions. In some examples, the processor is configured to perform such actions based in instructions located in memory 42. Additionally or alternatively, processor 40 may include internal or dedicated memory separate from memory 42.

In the example shown in FIG. 2, the set of electrodes 24 includes electrodes 24A, 24B, 24C, and 24D, and the set of electrodes 26 includes electrodes 26A, 26B, 26C, and 26D. In some embodiments, adjacent electrodes (e.g., 24A, 24B) are separated by at least 1 millimeter (mm), and in some embodiments, at least 1.5 mm. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48. As described, in some examples, IMD 16 does not include stimulation generator 44, and is configured for monitoring and diagnostic purposes.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12.

Although sensing module 46 is incorporated into a common housing with stimulation generator 44 and processor 40 in FIG. 2, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

The foregoing discusses various stimulation parameters used to deliver stimulation, including the frequency of the stimulation waveform, which may be, in one example, any frequency between 0 Hz and 500 Hz (e.g., in one specific example 130 Hz). Such a stimulation signal or waveform may comprise frequency components at a variety of frequencies. For instance, a pulsatile signal delivered at 130 Hz may comprise signal components including a primary frequency of 130 Hz and various harmonics or sub-harmonics of the primary frequency component. As will be appreciated, in some embodiments, any of a variety of signal shapes or waveforms having a primary frequency may be used.

It will be appreciated that, as referenced herein, a stimulation signal "including a stimulation frequency" refers to frequency content of the stimulation signal unless otherwise specified. That is, a signal applied "at a stimulation frequency" refers to a stimulation signal having frequency content including that stimulation frequency. As described herein, applying a stimulation signal at a stimulation frequency within a first frequency range or band does not preclude the stimulation signal from having frequency content outside of the first frequency range. That is, if a stimulation signal comprises a primary frequency, F, within a first frequency range or frequency band, the stimulation signal may include harmonics or sub-harmonics of F that need not fall within the first frequency range. The stimulation signal may additionally or alternatively comprise frequency content outside of the first range of frequencies that is not a harmonic or sub-harmonic of F without departing from the scope of the disclosure.

In some instances, sense signals received by the sensing module 46 can include signals of interest within a second range of frequencies that is separate from the first range of frequencies including components of the stimulation signal. In some embodiments, the signals of interest in the sense signals can include signals within the beta band. The beta band may include a frequency range of about 10 Hertz (Hz) to about 35 Hz, such as about 10 Hz to about 30 Hz or 13 Hz to about 30 Hz. Other signals of interest can include additional or alternative frequency bands, such as delta (e.g., less than approximately 4 Hz), theta (e.g., between approximately 4 Hz and approximately 8 Hz), alpha (e.g., between approximately 8 Hz and approximately 13 Hz), gamma (e.g., between approximately 35 Hz and approximately 100 Hz), or other known neurological frequency bands. In some examples, signals of interest are not limited to any one neurological frequency band, but can more generally be contained within a second frequency band which includes a range of frequencies overlapping with at least one neurological frequency band.

Signals of interest can include a variety of frequency bands according to the patient and the patient's condition. For instance, for certain patients (e.g., patients with Parkinson's disease), signals in the beta frequency band can be of particular interest to a clinician or physician observing the sense signals. However, neural signals can have a relatively low magnitude, for example in the microvolt ($\mu$V) range, and as a result can be difficult to analyze. Accordingly, in some examples, the sensing module 46 can include a signal chain comprising a variety of components for processing the signals received from one or more sensing electrodes or sense electrode combinations. For example, the sensing module 46 can include one or more pre-amplifiers, amplifiers, filters, analog-to-digital converters (ADC's), and the like. Such components can assist in the analysis of the sensed signals of interest by improving or maximizing the fidelity of the sensed signals. In some cases, this processing includes processing the sensed signal to extract signal components within one or more frequency bands of interest.

As described previously, a stimulation signal can be applied to a patient's brain or other tissue at one or more stimulation frequencies within a first range of frequencies. According to various therapy parameters, various properties of stimulation signals may include select electrode combination and polarity, pulse amplitude, pulse width, duty cycle, and frequency. In various treatment programs, stimulation pulses are intended to affect the bioelectrical signals in the patient, such as to suppress or promote such signals. For example, a stimulation signal can be applied to the patient's brain via at least one stimulation electrode (e.g., a unipolar stimulation electrode, a stimulation electrode combination, etc.) comprising one or more frequencies in order to achieve some physiological effect. This physiological effect may be indicated by a change in the frequency content of a sensed signal, such as a reduction in magnitude of the frequency content in one or more frequency ranges. For instance, a sensed signal in the time domain may be converted to the frequency domain so that the spectral power density within various frequencies bands within that time domain signal can be determined. In some examples, the power of the signal in the beta band may be an indication of the efficacy of stimulation for patient's suffering from some movement disorders. Stimulation may affect (e.g., reduce) the power of the signal in the beta band for such patients.

Accordingly, it can be advantageous to monitor the bioelectrical signals within the patient's brain or other nervous tissue while simultaneously applying a stimulation signal in order to observe the effect of one on the other. That is, sensing the sense signal from at least one sensing electrode while simultaneously applying a stimulation signal via at least one stimulation electrode can provide real time feedback of the efficacy of the applied stimulation signal. In addition, simultaneously monitoring sense signals while applying stimulation signals can provide information regarding the level of stimulation required for effective promotion or suppression of signals of interest as well as indicate potential side effects of the stimulation on the patient.

In some cases, the stimulation signal may be such that one or more frequency components thereof are outside of the frequency band of interest for sensing so that stimulation artifacts are not present, or are minimized, in the sensed signal. For instance, in some examples, the stimulation signal includes frequency components within a first range of frequencies that does not overlap with the second range of frequencies. This can be done in order to limit interference between the stimulation signal and sensed signals of interest. By analyzing the frequency content of the resulting sense signal, signals of interest in the second range of frequencies can be analyzed independently from artifacts from the stimulation signal in the first range of frequencies. In other instances, the first and second frequency ranges may overlap, in which stimulation signals may have similar frequency content as signals of interest.

As discussed, in some instances, the magnitude of signals of interest in the sense signal, such as particular frequency components in second range of frequencies, for example, can be relatively small. The sense signal can be processed to create a processed signal, which can facilitate analysis of the signals of interest. For example, the sensing module 46 can include at least one amplifier for amplifying the received sense signal. In various embodiments, the at least one amplifier can be configured to amplify any portion of the sense signal. For example, the at least one amplifier can amplify the entire received sense signal or only certain frequencies of the received sense signal, such as frequency components of interest in the second frequency band. In the latter case, a band-pass filter may be used to extract the frequencies of the received sense signal that are of interest (e.g., the signal components residing within the beta band). In some examples, amplification of the sense signal is a function of frequency of the received sense signal. In further examples, frequencies within the second range of frequencies are amplified more than the frequencies in the first range of frequencies. Additionally or alternatively, a transformation may be performed on the sense signal, such as a Fourier transform, to convert the signal to the frequency domain so that specific frequency components can be analyzed, as is discussed further below.

Amplification of the sense signal can lead to increased ability to analyze the efficacy of the stimulation signal on the patient. However, excessive amplification can result in the obscuring of data, rendering the amplified sense signal unreliable. For example, if the amplification of the sense signal is too high, the signal chain can become saturated, resulting in a potentially misleading processed signal. In some instances, when saturation occurs, the processed signal might indicate that the signals of interest are responding to stimulation as desired when in reality the observed change in the processed signal is an artifact of the saturation and the patient is not actually receiving adequate treatment. In other instances, saturation may result in disguised changes in the signals of interest, leading to a misrepresentation that the patient is not receiving adequate treatment. To compensate for some such instances, aspects of the stimulation signal may be unnecessarily adjusted beyond a desired magnitude in order to achieve observable changes in the signals of interest. In general, saturation can lead to a variety of undesirable circumstances, such as a lack of therapy provided to a patient, an abundance of unnecessary therapy provided to the patient, which can drain the power source unnecessarily or lead to side effects in the patient, or a generally unusable signal from which a conclusion cannot be reached.

Accordingly, it can be advantageous to determine when saturation of the signal chain occurs so that it is known that the processed signal is unreliable and measures can be taken to eliminate the saturation. In some cases, it can be determined that the signal chain is saturated based on operating characteristics of components in the signal chain. For instance, saturation may be evidenced by a pre-amp being over range or by problems in a slew rate of an analog-to-digital converter (ADC). In some embodiments, the system (e.g., via the processor 40 or other components of the IMD 16) can automatically perform at least one action in response to a detected saturation. Such actions can include, in some examples, any combination of placing the system in a safe mode in which one or more system actions (e.g., applying a stimulation pulse) are disabled, reducing the gain of at least one amplifier, adjusting the operation of one or more additional signal chain components, adjusting at least one property of the stimulation signal, adjusting which of electrodes 24, 26 are used as stimulating and sensing electrodes, adjusting the impedance of at least one sensing electrode as described in the patent application Ser. No. 14/726,028 entitled "IMPEDANCE MATCHING AND ELECTRODE CONDITIONING IN PATIENT INTERFACE SYSTEMS," filed May 29, 2015, which is hereby incorporated herein by reference in its entirety, storing an indication in memory indicating potential saturation for use in analyzing any stored sensed signal, and/or providing some notification to a user (e.g., a clinician or patient). In some examples, a combination of actions can be performed. For example, in response to detected saturation, the system can enter a safe mode while adjusting the gain of an amplifier in the signal chain. Once the amplification is adjusted, the system may exit the safe mode and operate normally. In some systems, in the event that lower the gain is not an effective course of action for eliminating saturation, the system may remain in safe mode until appropriate action is taken. Automatic performance of the at least one action can be initiated, for example, according to operating instructions 58 stored in memory 42 communicating with the processor 40.

In some embodiments, the electrodes 24, 26 of therapy system 10 can include at least one test electrode (or similarly, test electrode combination) configured to apply a test tone signal to the patient's brain. The test tone electrode can receive a test signal from, for example, the stimulation generator 44. In other examples, the IMD 16 can include a separate test tone module 50 configured to generate the test tone signal for application to the brain tissue via the test tone electrode. The test tone signal can have a test tone frequency that is generally distinguishable from both a stimulation signal and sensed signals of interest. For example, the test tone signal may include a test tone frequency that is not in the first range of frequencies (including the stimulation frequency) or the second range of frequencies (frequency content of signals of interest). For instance, in some embodiments, the stimulation signal can include a stimulation frequency content between approximately 120 Hz and 500 Hz (e.g., within a first range of frequencies; as described, various harmonics and sub-harmonics of the stimulation frequency may depart from this range), the second frequency range can be between approximately zero Hz and 100 Hz, and the test tone frequency can be approximately 105 Hz. It will be appreciated that in the present example, test tone frequencies between 100 Hz and 120 Hz are appropriately not contained in the first or second frequency ranges and are also possible. It may also be that various harmonics and sub-harmonics of the test tone frequency may fall within one or both of the first and second frequency ranges. In still further embodiments, the test tone can be within one of the first and second frequency bands yet distinguishable from the stimulation signal or the signals of interest in the sense signal.

In some embodiments, the stimulation generator 44 is configured to generate a stimulation signal having a built-in test tone signal. That is, the stimulation pulse can include a stimulation signal having frequencies within the first frequency band and a test tone frequency component that is outside of the first frequency band. In such embodiments, the test tone electrode can be the same electrode as the stimulation electrode (or stimulation electrodes or stimulation electrode combination), and the test tone is provided by the stimulation generator 44.

The sense signal received by the sensing module can include frequency content having the test tone frequency resulting from the applied test tone signal. Because the test tone frequency is outside of the first and second frequency bands, the received sense signal (or the resulting processed signal from the signal chain) can include distinguishable information regarding the first frequency band, the second frequency band and signals of interest contained therein, and the test tone frequency.

During simultaneous stimulation and sensing, the test tone frequency can be observed in addition to the signals of interest in the processed signal. The test tone signal can be such that, in the event of signal chain saturation, the magnitude of the test tone frequency content of the processed signal decreases, and in some cases, sub-harmonics of the test tone frequency are created. Accordingly, aspects of the processed signal can be analyzed to determine the occurrence of saturation of the signal chain. It will be appreciated that as described herein, analysis of the sense signal can include analysis of the processed signal and is not limited to describing only an unprocessed signal received from sense electrodes unless specifically stated.

Figure 3:
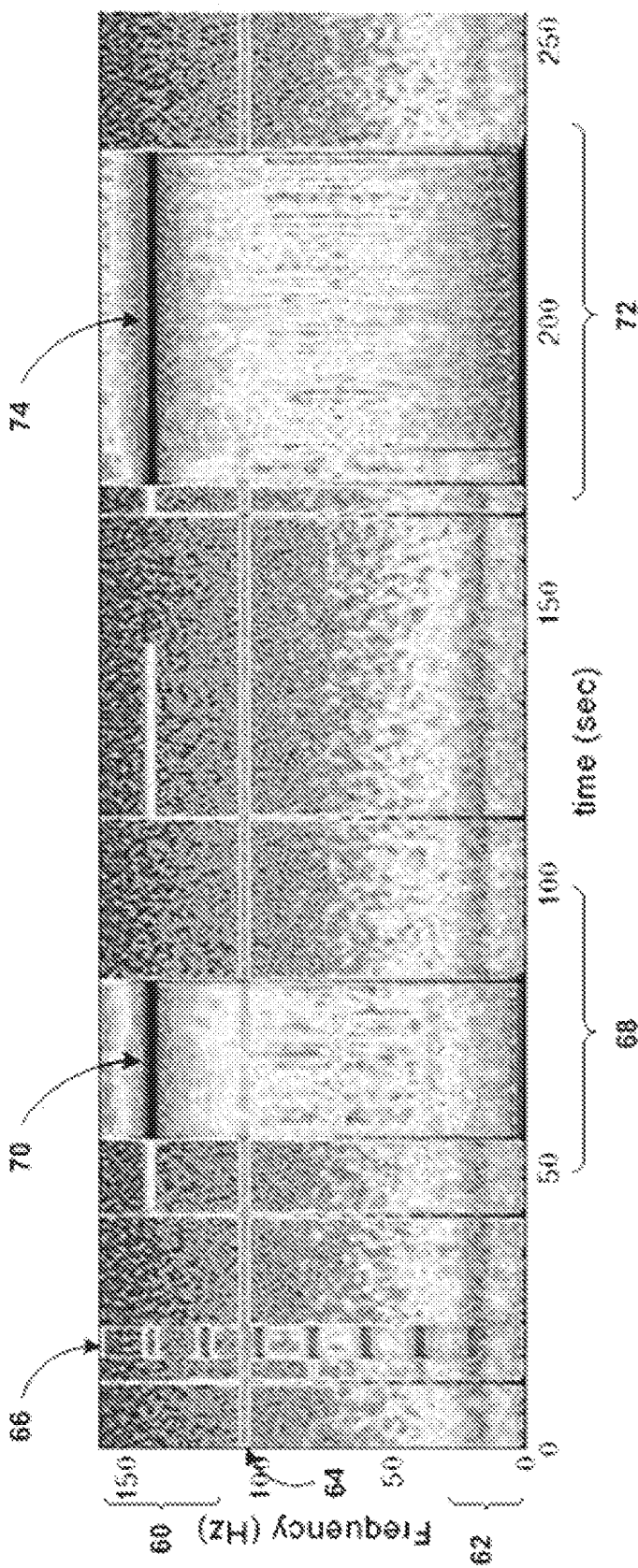
FIG. 3 is an example spectrogram of a bioelectrical brain signal sensed within a brain of a patient.

The received sense signal can be processed and data from the sensed signal can be saved in memory 42 for analysis. In some examples, data can be captured over time and displayed as a spectrogram. FIG. 3 is an example spectrogram of bioelectrical brain signals of a human subject which shows the frequency content of the sensed time domain signal. This can be generated in several ways, such as by applying a Fourier transform to the sensed time domain signal or by processing the sensed time domain signal using a series of bandpass filters. The y-axis of the spectrogram indicates the frequency band of the bioelectrical brain signal, the x-axis indicates time, and the z-axis, which extends substantially perpendicular to the plane of the image of FIG. 3 and is generally represented by the color of the spectrogram, indicates a power level of the bioelectrical brain signal. The spectrogram provides a three-dimensional plot of the energy of the frequency content of a bioelectrical brain signal over time.

As shown in the exemplary spectrogram of FIG. 3, stimulation pulses 70, 74 are applied at various times in a first frequency band 60. A test tone signal 64 is shown having a frequency component (e.g., a test tone frequency) of approximately 105 Hz. Additional signals are at times present in a second frequency band 62. Such signals can correspond to bioelectrical signals in the patient' brain. Optionally, a distinct synchronization pulse 66 is emitted to assist in temporal alignment of data across multiple sensing and application procedures.

The spectrograph of FIG. 3 can indicate to a clinician or other user the efficacy of treatment to a patient over a period of time. For instance, the spectrograph includes data from a first time period 68 between approximately 50 seconds and 100 seconds during which a stimulation signal 70 is applied having a frequency in a first frequency band 60. During the application of the stimulation signal 70, signals in a second frequency band 62, in this instance signals at approximately 10-20 Hz, are seemingly suppressed. In addition, during the application of the stimulation signal 70, the test tone frequency 64 remains present in the spectrograph, indicating that saturation has likely not occurred and that the sense signal during that time period is reliable. Thus, the signals in the second frequency band 62 were likely suppressed due to the application of the stimulation signal 70. In another instance, the spectrograph includes data from a second time period 72, between approximately 175 and 225 seconds, in which another stimulation signal 74 is applied. During the second time period 72, the test tone frequency 64 disappears from the sense signal, indicating that data from the second time period 72 may not be reliable due to signal chain saturation.

Figure 4:
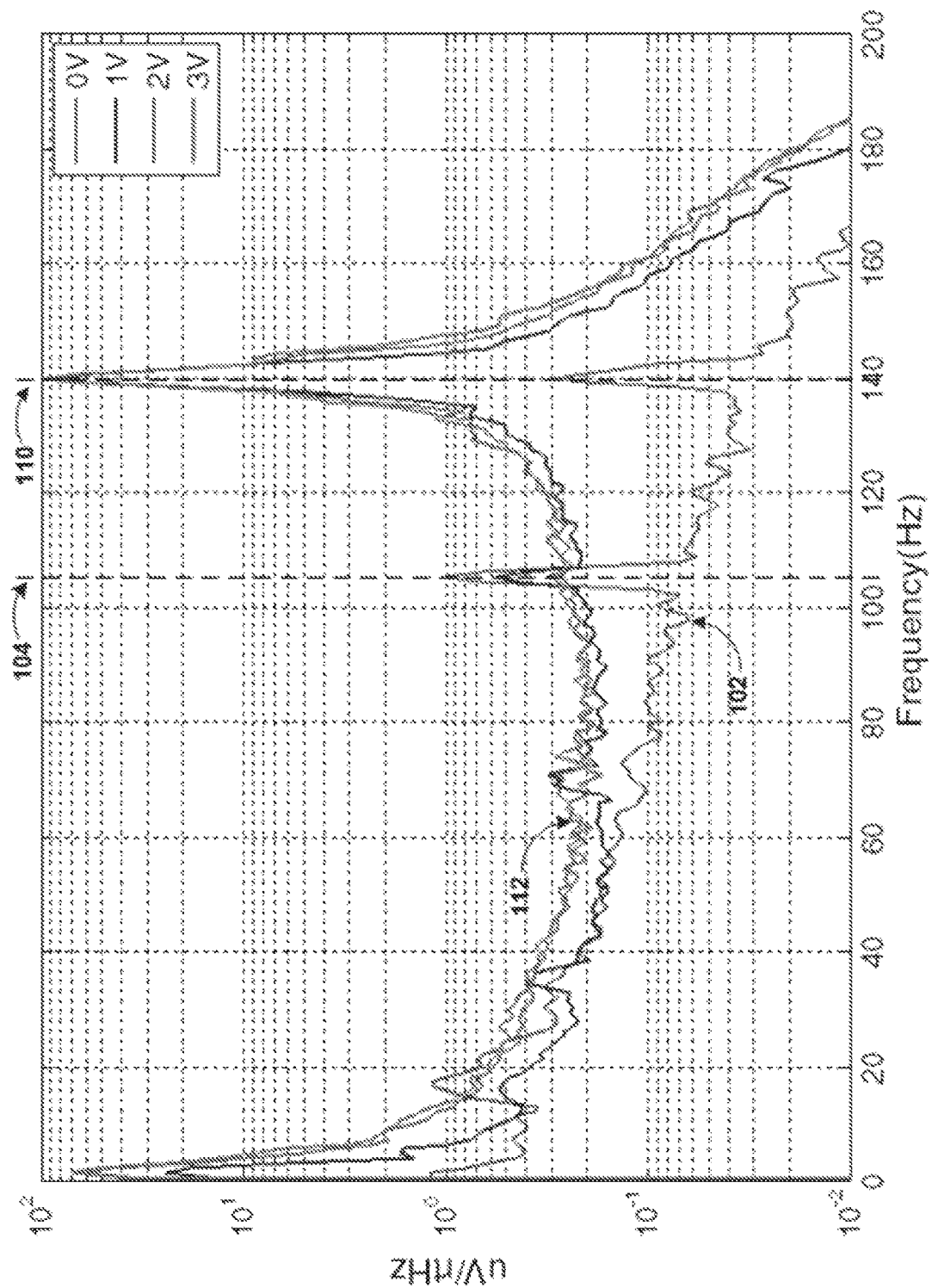
FIG. 4 is a conceptual power spectral density plot of bioelectrical signals in a DBS system in which saturation is present.
Figure 5:
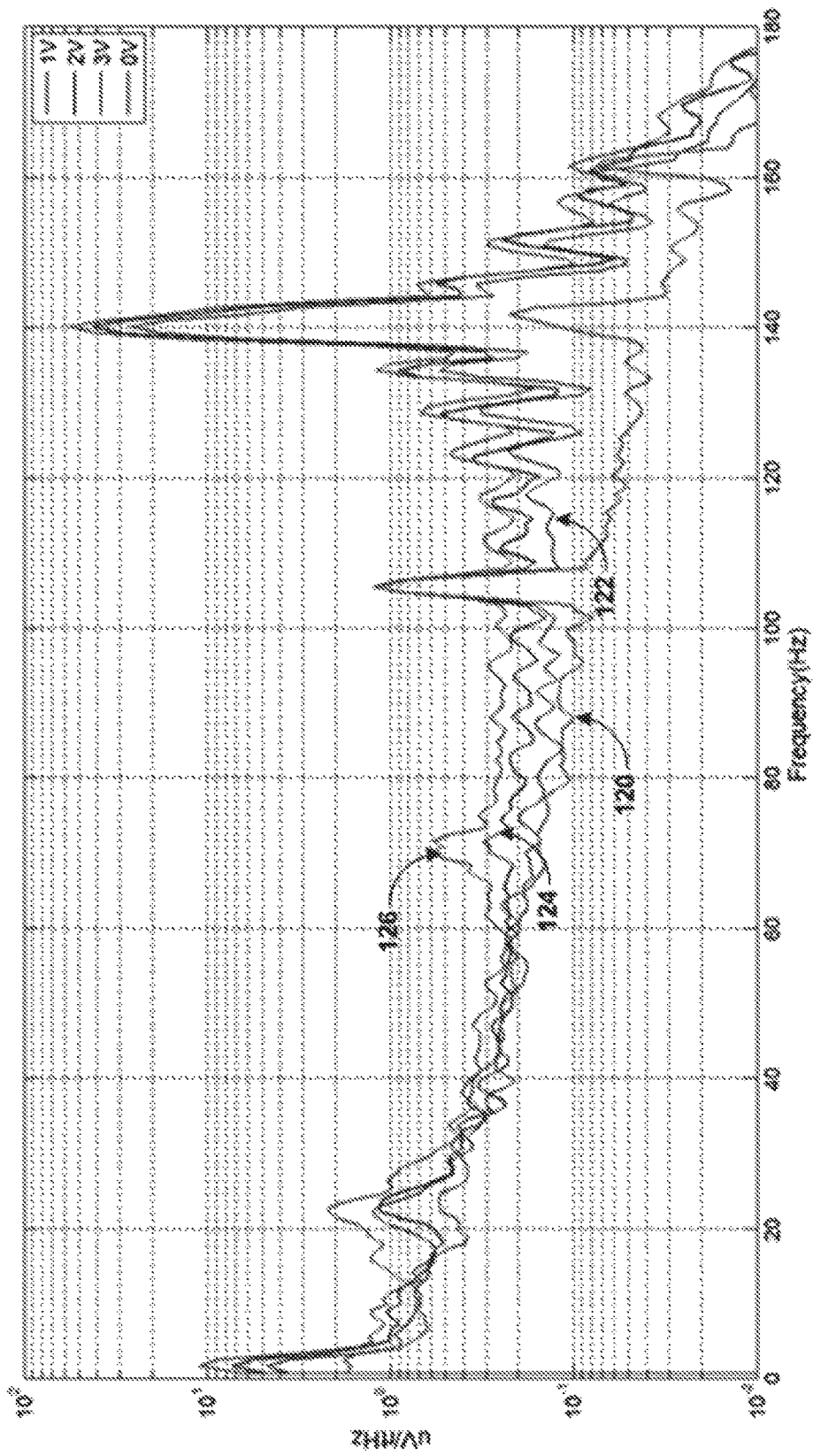
FIG. 5 is a conceptual power spectral density plot of bioelectrical signals in a DBS system free from saturation.

As described, data from the spectrograph of FIG. 3 includes information regarding time, frequency, and amplitude of sense signals. Subsets of such data can be helpful for providing useful analysis. For example, a slice of a spectrograph in the x-z plane can provide information regarding the magnitude of a particular frequency in the sense signal over time. Alternatively, a slice of the spectrograph in the y-z plane can provide the spectral content of the sense signal at a particular time. FIGS. 4 and 5 are exemplary slices in the y-z plane of such a spectrograph, illustrating spectral content of a sense signal at a single point in time.

FIG. 4 is a sample plot illustrating the frequency content of a sense signal sensed during the application of stimulation pulses at varying magnitudes and corresponding adjustments in the processing of the sense signal. The Y axis provides the amplitude of a sensed signal in uV/rtHz. In the illustrated example, the test tone frequency is approximately 105 Hz, and the stimulation frequency has frequency content within the first range of frequencies (approximately 140 Hz). A first signal 102 is shown as having prominent peaks at 105 Hz (corresponding to the test tone frequency 104) and 140 Hz (corresponding to the stimulation frequency 110). Lower-frequency content (e.g., approximately 18 Hz) in the illustrated sense signal can include signals of interest, such as the beta band component of the bioelectrical signals in the patient's brain. As shown, the test tone frequency 104 is clearly present in the first signal 102.

FIG. 4 includes a second signal 112 observed at a separate time than first signal 102. The second signal 112 has a large peak at the stimulation frequency (approximately 140 Hz) and shows little activity in the second frequency band (e.g., approximately 0 Hz to 100 Hz). However, the second signal 112 does not have a clear peak at the test tone frequency 104 (approximately 105 Hz), indicating that saturation may have occurred. Accordingly, an observed change from detected activity in the second frequency band in the first signal 102 to an absence of detected activity in the second frequency band in the second signal 112 cannot be reliably attributed to suppression of the activity in the second frequency band because saturation has occurred.

As described, in some embodiments, the system can automatically perform at least one action in response to detected saturation. Thus, the system can monitor the presence of the test frequency in the sense signal, and, in the event that the test frequency component of the sense signal drops below a predetermined threshold, the system can detect saturation and automatically perform at least one action. In various examples, when the test frequency component falls below a predetermined threshold, the system can adjust at least one of the stimulation signal, the test tone signal, and the processing of the sense signal (e.g., reducing the gain of at least one amplifier). Performing the at least one corrective action can result in the detection of the test frequency in the sense signal, and accordingly an indication that other information from the sense signal is reliable.

As previously described, saturation of the signal chain can additionally or alternatively result in the appearance of sub-harmonics of the test frequency being present in the sense signal. Accordingly, in some embodiments, saturation of the signal chain can be detected by observing the sub-harmonics of the test frequency present in the sense signal. In the event that a sub-harmonic (or in some embodiments, a combination of sub-harmonics) exceeds a predetermined threshold, saturation is detected. Similarly to the above embodiments, the detection of saturation can cause the system to perform at least one action.

It will be appreciated that, while a variety of methods for detecting saturation have been described, any one method or combination of such methods can be employed by a system according to various embodiments. For example, a system can perform any combination of monitoring operation of components of the signal chain, observing the test frequency in the sense signal, and observing the sub-harmonics of the test frequency present in the sense signal. In various embodiments, any one such method can be used to detect saturation. In alternative embodiments, saturation is detected when more than one such events is observed. In general, saturation can be detected based on any individual or combination of appropriate methods, in some embodiments triggering at least one corrective action such as those previously discussed.

Similar to FIG. 4, FIG. 5 is a sample plot illustrating the frequency content of a sense signal while simultaneous stimulation pulses of varying magnitudes are applied. However, in the stimulation events of FIG. 5, saturation is avoided. As shown, as a variety of stimulation pulses are applied at a stimulation frequency (approximately 140 Hz) along with a test tone signal having a test tone frequency (approximately 105 Hz). The stimulation frequency and test tone frequency are present in the processed sense signal. Sense signals also have frequency content in a second frequency band (e.g., approximately 0-100 Hz, or approximately 10-30 Hz). In a first signal 120 corresponding to a 0V stimulation pulse, a noticeable peak near 22 Hz is shown. A second signal 122 corresponding to a 1V stimulation pulse shows a reduction in the magnitude at the same frequency, as does a third signal 124 corresponding to a 2V stimulation pulse. Finally, a fourth signal 126 corresponding to a 3V stimulation pulse shows a minimal peak at the same frequency in the second frequency band (approximately 22 Hz). Comparisons of the first 120 through fourth 126 signals indicate that increasing the magnitude of the stimulation pulse from 0V to 3V suppresses bioelectrical signals in the second frequency band. Moreover, because the test tone frequency is clearly present in each of the first 120 through fourth 126 signals, it is likely that the signal chain did not saturate, and that the observed suppression in the second frequency band while simultaneously applying a stimulation signal is reliable.

Figure 6:
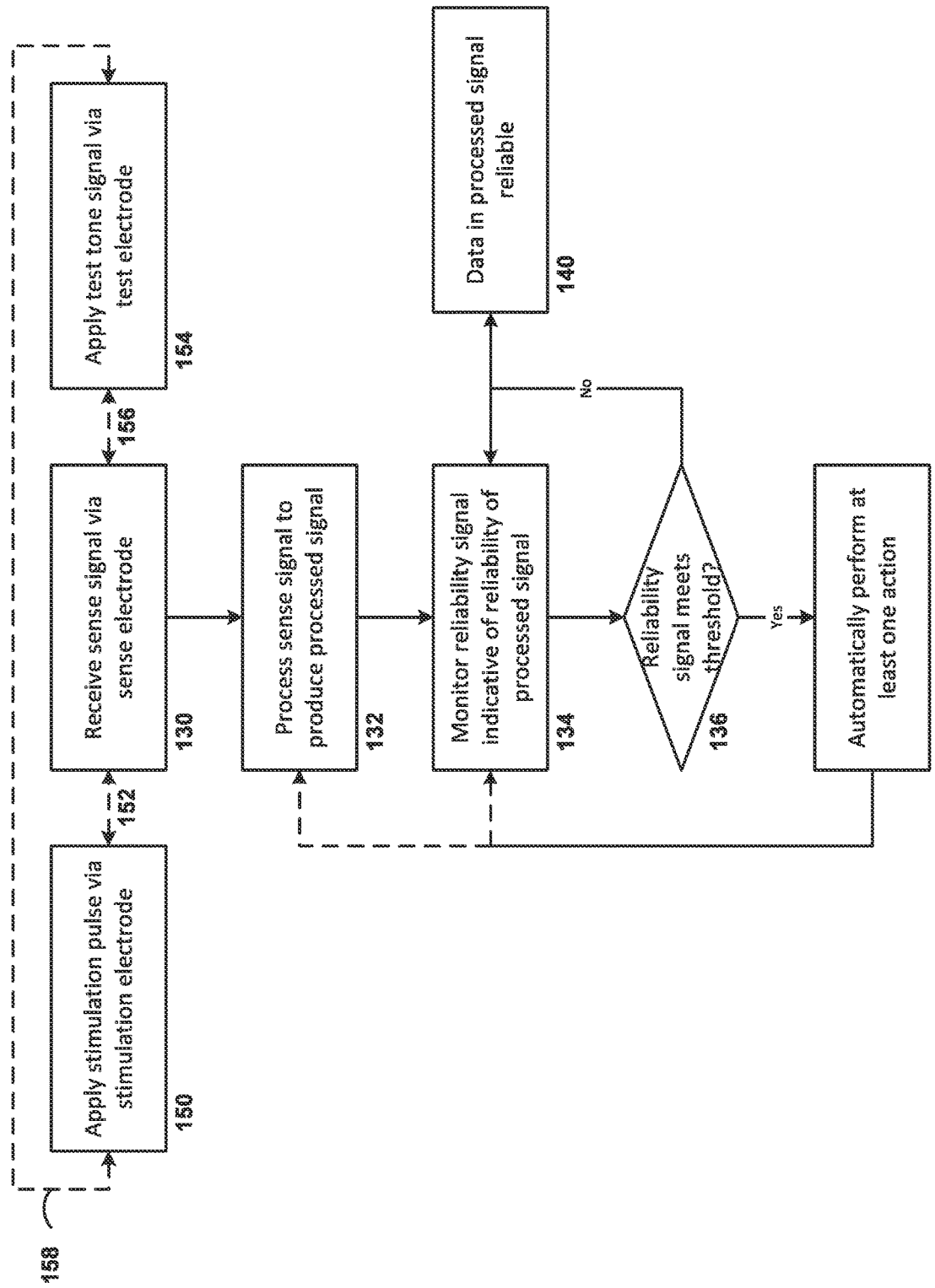
FIG. 6 is a flow diagram illustrating an exemplary technique for detecting and addressing saturation in a DBS system.

FIG. 6 is a process-flow diagram illustrating an exemplary process monitoring saturation of a signal chain in a DBS system. The process includes receiving a sense signal via a sense electrode (130). In general, as discussed, the sense electrode can include a single electrode, a plurality of electrodes, an electrode combination, or the like. Some embodiments of the method include one or both of the steps of applying a stimulation pulse via a stimulation electrode (150) as shown by broken line 152, and applying a test tone signal via a test electrode (154) as shown by broken line 156. Similarly, the stimulation electrode and the test electrode can include a single electrode, a plurality of electrodes, an electrode combination, or the like. In some embodiments, the test tone signal can be included in the stimulation pulse, as indicated by broken line 158. In some such embodiments, the stimulation electrode(s) and the test electrode(s) can include some of all of the same electrode(s). As previously described, the stimulation pulse can be contained in a first frequency band while the test tone signal can include a test tone frequency that is outside of the first frequency band.

The process further includes processing the sense signal to produce a processed signal (132). Processing the signal can include steps of, for example, filtering and amplifying the sense signal. Processing can also include performing a transform of the signal (e.g., a Fourier transform) such as to determine the amplitude of various frequency components of the signal. The process can include monitoring a reliability signal indicative of the reliability of the processed signal (134). As described, such a reliability signal can include the presence of a test tone frequency in the processed signal, the presence of sub-harmonics of the test tone frequency in the processed signal, or any of a variety of attributes of components in the signal chain.

The system (e.g., via the processor 40) can determine whether or not the reliability signal meets a predetermined threshold (136). For instance, the system can determine if the test tone frequency has a magnitude below a predetermined level, if sub-harmonics of the test tone frequency exceed a predetermined threshold, or if components of the signal chain have attributes that meet predetermined thresholds. In one example, the magnitude may be the power level in a particular frequency or frequency band in the processed signal. If it is determined that the reliability signal does not meet a predetermined threshold, the system continues to monitor the reliability signal (134) and determines that the data in the processed signal is reliable (140).

On the other hand, if it is determined that the reliability signal does meet a predetermined threshold, the system can automatically perform at least one action (142). Performing the at least one action can act to adjust the processed signal so that the reliability signal does not meet the threshold. Performing the at least one action can include, for example, placing the system in a safe mode, adjusting the gain of an amplifier in the signal chain, adjusting the stimulation signal, adjusting the test tone signal, or adjusting at least one additional or alternative aspect of the stimulation or the sensing modules. As shown in the illustrated diagram of FIG. 6, since performing the at least one action can result in adjusting the processing of the sense signal, the system can, after performing the at least one action, process the sense signal (132). In other embodiments, in the event the processing step is not changed, the system can, after performing the at least one action, continue to monitor the reliability signal (134).

It will be appreciated that the process illustrated in the diagram of FIG. 6 is exemplary and does not represent every possible method of carrying out or utilizing the invention. Rather, various steps in the process can be omitted, permuted, or performed substantially simultaneously without departing from the scope of the invention. For example, in some embodiments, the system may apply a test tone signal via a test electrode (154) and receive sense signals via sense electrode (130), process the received sense signal and compare a reliability signal to a threshold to ensure that pre-therapy measurements are reliable prior to applying a stimulation pulse. Additionally or alternatively, a variety of threshold comparisons may be used to analyze the reliability signal. In various embodiments, saturation may be detected if a particular signal drops below a predetermined threshold level, rises above a predetermined threshold level, or meets a predetermined threshold level. That is, "meeting a threshold" does not require that a reliability signal increases beyond a certain point. For instance, in some embodiments, a reliability signal meets a threshold and results in the system automatically performing at least one action when the magnitude of the test tone frequency falls to or below a predetermined threshold. In general, any appropriate reliability signal comparison may be used.

In addition, the system can perform additional steps based on a variety of determinations during the execution of the process of FIG. 6. In some embodiments, in the event that the system determines that the signal chain is saturated, the system can automatically perform at least one action and save the at least one action performed in memory 42. For example, in the event that saturation is detected, the system can reduce the gain of at least one amplifier in the signal chain, and save the relevant gain information (e.g., combinations of the previous gain, new gain, gain change, etc.) to memory 42.

In some embodiments, the system can perform a calibration step prior to operation. In such a process, the system can monitor the processed sense signal for evidence of saturation, and adjust the gain of at least one amplifier in the signal chain until the system determines the maximum gain without inducing saturation of the signal chain. The maximum gain can be saved to memory 42 and used as a starting gain for subsequent therapy procedures. In some examples, a gain value saved in memory can be applied at the start of all future therapy sessions. In other examples, the gain value can be applied for a set number of therapy sessions before another calibration is performed. In still further embodiments, a calibration step can be performed at the beginning of every therapy session.

While the foregoing contemplates use of a sensing mechanism along with the delivery of stimulation to monitor the functionality of the signal chain (e.g., to determine whether amplifiers are becoming saturated), the techniques described herein may also be used to detect saturation in the absence of stimulation. For instance, movement of a patient may cause spikes in the detected signals that result in the saturation of the sensed signals. Use of the disclosed techniques can detect this saturation and provide adjustments to the signal chain (e.g., adjustments to the amplifier gain) so that sensing can continue uninterrupted even when the patient is moving. This type of sensing and adjustment can occur with, or without stimulation. Thus, while examples above describe sensing during stimulation, the techniques described herein are not so limited, and can be used in the absence of the delivery of stimulation to improve signal sensing capability.

It will be appreciated that various operating steps of the system can be carried out manually or automatically. For example, a clinician, patient, or other system operator can interface with the system via programmer 14 or other external device as described in U.S. Pat. No. 8,428,733, which is incorporated by reference. In such examples, the system operator can observe evidence of saturation in processed sense signals and initiate appropriate action to eliminate the saturation. In other examples, the processor 40 can access information stored in any one or combination of operating instructions 58 and therapy programs 54 in memory 42 of the system to automatically detect the occurrence of saturation and to take appropriate action.

Various examples of the disclosure have been described. While many described embodiments included system for stimulating and sensing from a patient's brain tissue, these are not intended to limit the scope of the invention. For instance, the foregoing techniques can be used in system for only sensing, such as purely diagnostic system. Additionally or alternatively, systems can be used in other physiological sensing applications, such as neural tissue outside of the brain, muscle tissue, etc. These and other examples are within the scope of the following claims.

The invention claimed is:
1. A method of monitoring physiological activity comprising:
applying, by a processor, a test tone signal to a patient via at least one test electrode, the test tone signal having a test tone frequency;
receiving, by the processor, a sense signal from the patient via at least one sense electrode, wherein the received signal comprises a first component at the test tone frequency and a second component indicative of physiological activity of the patient;
amplifying the received sense signal via at least one amplifier, wherein the amplified sense signal comprises a third component at the test tone frequency and a fourth component indicative of physiological activity of the patient;
detecting a magnitude of the third component of the amplified sense signal at the test tone frequency; and
in response to the magnitude dropping below a predetermined threshold, reducing, by the processor, the gain of the at least one amplifier.

2. The method of claim 1, further comprising:
applying, by the processor, a stimulation signal to the brain via at least one stimulation electrode; and
determining, by the processor, a change in the amplified sense signal indicative of promoted or suppressed physiological activity based on the applied stimulation signal.

3. The method of claim 2, wherein applying the stimulation signal to the patient comprises applying a stimulation signal comprising a primary frequency located in a first frequency band, wherein the test frequency is outside the first frequency band.

4. The method of claim 3, wherein determining a change in the amplified sense signal indicative of promoted or suppressed physiological activity comprises determining the magnitude of the fourth component of the amplified sense signal in a second frequency band, wherein the second frequency band is distinct from the first frequency band, and wherein the test frequency is outside of the first and second frequency bands.

5. The method of claim 4, further comprising:
determining, by the processor, an amount of promotion or suppression of the physiological activity in the second frequency band;
comparing, by the processor, the amount of promotion or suppression to a minimum response threshold; and
in response to the amount of promotion or suppression of the physiological activity being below the minimum response threshold, increasing, by the processor, the magnitude of the applied stimulation signal.

6. The method of claim 1, wherein:
applying the test tone signal to a patient comprises applying the test tone signal to the patient's brain; and
the physiological activity comprises brain activity.

7. The method of claim 6, further comprising generating, by the processor, a graphical display for user analysis, the graphical display including representation of the frequency content of the received sense signal over time.

8. A system for providing and confirming treatment to a patient comprising:
at least one test electrode configured to apply a test tone signal to a patient, the test tone signal having a test tone frequency;
at least one sense electrode configured to receive a sense signal via at least one sense electrode, wherein the received signal comprises a first component at the test tone frequency and a second component indicative of physiological activity of the patient;
at least one amplifier configured to amplify the received sense signal, wherein the amplified sense signal comprises a third component at the test tone frequency and a fourth component indicative of physiological activity of the patient,
wherein the system further comprises one or more processors configured to:
detect the magnitude of the third component of the amplified sense signal at the test tone frequency; and
in response to the magnitude dropping below a predetermined threshold, reduce the gain of the at least one amplifier.

9. The system of claim 8, wherein the one or more processors are further configured to:
apply a stimulation signal to the brain via at least one stimulation electrode; and
determine a change in the amplified sense signal indicative of promoted or suppressed physiological activity based on the applied stimulation signal.

10. The system of claim 9, wherein to apply the stimulation signal to the patient, the one or more processors are configured to apply a stimulation signal comprising a primary frequency located in a first frequency band, wherein the test frequency is outside the first frequency band.

11. The system of claim 9, wherein the one or more processors are further configured to:
determine an amount of promotion or suppression of the physiological activity in a second frequency band wherein the second frequency band is distinct from the first frequency band, and the test frequency is outside of the first and second frequency bands;
compare the amount of promotion or suppression to a minimum response threshold;
determine that the amount of promotion or suppression of the physiological activity is above or below the minimum response threshold; and
output an indication that the amount of promotion or suppression of the physiological activity is above or below the minimum response threshold.

12. The system of claim 8, wherein to output an indication, the one or more processors are configured to generate a graphical display for user analysis, the graphical display including representation of the frequency content of the sense signal over time.

13. The system of claim 8, wherein to reduce the gain of the at least one amplifier, the one or more processors are further configured to incrementally lower the gain until the magnitude of the third component in the amplified sense signal at the test tone frequency until the third component of the amplified sense signal returns above the predetermined threshold.

14. The system of claim 8, wherein
to apply the test tone signal to a patient, the one or more processors are configured to apply the test tone signal to the patient's brain; and
the physiological activity comprises brain activity.

15. An implantable device for providing and confirming treatment to a patient, the device comprising:
at least one test electrode configured to apply a test tone signal to a patient, the test tone signal having a test tone frequency;
at least one sense electrode configured to receive a sense signal via at least one sense electrode, wherein the received signal comprises a first component at the test tone frequency and a second component indicative of physiological activity of the patient;
at least one amplifier configured to amplify the received sense signal,
wherein the device further comprises one or more processors configured to:
detect the magnitude of the first component of the amplified sense signal at the test tone frequency; and
in response to the magnitude dropping below a predetermined threshold, reduce the gain of the at least one amplifier.

16. The device of claim 15, wherein the one or more processors are further configured to:
apply a stimulation signal to the brain via at least one stimulation electrode;
determine a change in the amplified sense signal indicative of promoted or suppressed physiological activity based on the applied stimulation signal; and
output an indication of the determined change.

17. The device of claim 16, wherein to apply the stimulation signal to the patient the one or more processors are configured to apply a stimulation signal comprising a primary frequency located in a first frequency band, wherein the test frequency is outside the first frequency band.

18. The device of claim 16, wherein the one or more processors are further configured to:
determine an amount of promotion or suppression of the physiological activity in a second frequency band wherein the second frequency band is distinct from the first frequency band, and the test frequency is outside of the first and second frequency bands;
compare the amount of promotion or suppression to a minimum response threshold; and
determine that the amount of promotion or suppression of the physiological activity is above or below the minimum response threshold.

19. The device of claim 18, wherein the one or more processors is further configured to output an indication that the amount of promotion or suppression of the physiological activity is above or below the minimum response threshold, wherein the output comprises generating a graphical display for user analysis, the graphical display including representation of the frequency content of the sense signal over time.

20. The device of claim 15, wherein
to apply the test tone signal to a patient, the one or more processors are configured to apply the test tone signal to the patient's brain; and
the physiological activity comprises brain activity.

* * * * *